(12) United States Patent
Burkholz

(10) Patent No.: US 10,307,571 B2
(45) Date of Patent: *Jun. 4, 2019

(54) BI-DIRECTIONAL CANNULA FEATURE CAPTURE MECHANISM

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/216,313

(22) Filed: Jul. 21, 2016

(65) Prior Publication Data

US 2016/0325078 A1 Nov. 10, 2016

Related U.S. Application Data

(63) Continuation of application No. 13/939,575, filed on Jul. 11, 2013, now Pat. No. 9,399,120.

(51) Int. Cl.
*A61M 25/06* (2006.01)
*A61M 39/10* (2006.01)

(52) U.S. Cl.
CPC .... *A61M 25/0631* (2013.01); *A61M 25/0606* (2013.01); *A61M 25/0618* (2013.01); *A61M 39/10* (2013.01); *A61M 25/0693* (2013.01); *A61M 2039/1077* (2013.01)

(58) Field of Classification Search
CPC .......... A61M 25/0606; A61M 25/0612; A61M 25/0618; A61M 25/0631; A61M 39/0693; A61M 2039/064; A61M 2039/0633; A61M 2039/0626; A61M 2039/066; A61M 2039/0686

See application file for complete search history.

(56) References Cited

U.S. PATENT DOCUMENTS

| | | | |
|---|---|---|---|
| 4,952,207 | A | 8/1990 | Lemieux |
| 4,964,854 | A | 10/1990 | Luther |
| 5,085,648 | A | 2/1992 | Purdy et al. |
| 5,135,504 | A | 8/1992 | McLees |

(Continued)

FOREIGN PATENT DOCUMENTS

| | | |
|---|---|---|
| CN | 102387831 | 3/2012 |
| EP | 1 568 393 A1 | 8/2005 |

(Continued)

*Primary Examiner* — Jenna Zhang
(74) *Attorney, Agent, or Firm* — Kirton & McConkie; Craig Metcalf; Kevin Stinger

(57) ABSTRACT

A bi-directional cannula feature capture mechanism is described herein. Generally, the capture mechanism comprises an inner housing, an outer housing, and a cannula. The inner housing comprises a proximal and a distal cannula feature mating component. The outer housing is adapted to slidably receive the inner housing in a proximal direction. Additionally, the cannula extends through the inner housing and the cannula's feature has a proximal engagement and a distal engagement. The proximal and distal engagements are respectively configured to irreversibly engage the proximal and distal cannula feature mating components when the cannula tip is moved into a shielded position.

6 Claims, 11 Drawing Sheets

(56) References Cited

U.S. PATENT DOCUMENTS

| | | | |
|---|---|---|---|
| 5,405,323 A * | 4/1995 | Rogers | A61M 39/0693 604/167.04 |
| 5,601,536 A | 2/1997 | Crawford et al. | |
| 5,718,688 A * | 2/1998 | Wozencroft | A61M 5/3273 604/164.07 |
| 5,833,670 A * | 11/1998 | Dillon | A61M 25/0631 604/263 |
| 6,004,294 A | 12/1999 | Brimhall et al. | |
| 6,012,213 A | 1/2000 | Chang et al. | |
| 6,117,108 A | 9/2000 | Woehr et al. | |
| 6,224,569 B1 * | 5/2001 | Brimhall | A61M 25/0618 604/164.06 |
| 6,287,278 B1 | 9/2001 | Woehr et al. | |
| 6,322,537 B1 | 11/2001 | Chang | |
| 6,379,333 B1 | 4/2002 | Brimhall et al. | |
| 6,443,927 B1 | 9/2002 | Cook | |
| 6,443,929 B1 | 9/2002 | Kuracina et al. | |
| 6,616,630 B1 | 9/2003 | Woehr et al. | |
| 6,629,959 B2 | 10/2003 | Kuracina et al. | |
| 6,652,486 B2 | 11/2003 | Bialecki et al. | |
| 6,652,490 B2 | 11/2003 | Howell | |
| 6,663,592 B2 | 12/2003 | Rhad et al. | |
| 6,692,471 B2 | 2/2004 | Boudreaux | |
| 6,749,588 B1 * | 6/2004 | Howell | A61M 5/3273 604/110 |
| 6,761,706 B2 | 7/2004 | Vaillancourt | |
| 6,860,871 B2 | 3/2005 | Kuracina et al. | |
| 6,914,212 B2 | 7/2005 | Adams | |
| 7,002,098 B2 | 2/2006 | Adams | |
| 7,008,404 B2 | 3/2006 | Nakajima | |
| 7,160,269 B2 | 1/2007 | Woehr | |
| 7,186,239 B2 | 3/2007 | Woehr | |
| 7,214,208 B2 | 5/2007 | Vaillancourt | |
| 7,238,169 B2 | 7/2007 | Takagi et al. | |
| 7,264,613 B2 | 9/2007 | Woehr et al. | |
| 7,347,839 B2 | 3/2008 | Hiejima | |
| 8,496,623 B2 | 7/2013 | Burkholz | |
| 9,399,120 B2 | 7/2016 | Burkholz | |
| 2002/0128604 A1 * | 9/2002 | Nakajima | A61M 39/0693 604/164.01 |
| 2002/0169418 A1 | 11/2002 | Menzi et al. | |
| 2003/0144627 A1 | 7/2003 | Woehr et al. | |
| 2004/0010227 A1 | 1/2004 | Riesenberger et al. | |
| 2004/0186434 A1 | 9/2004 | Harding et al. | |
| 2004/0204681 A1 | 10/2004 | Thoresen et al. | |
| 2004/0225260 A1 | 11/2004 | Villa et al. | |
| 2004/0236288 A1 | 11/2004 | Howell et al. | |
| 2004/0243061 A1 | 12/2004 | McGurk | |
| 2005/0027263 A1 | 2/2005 | Woehr et al. | |
| 2005/0080378 A1 | 4/2005 | Cindrich et al. | |
| 2006/0116638 A1 | 6/2006 | Woehr et al. | |
| 2006/0270980 A1 | 11/2006 | Menzi et al. | |
| 2007/0093778 A1 * | 4/2007 | Cindrich | A61M 5/158 604/500 |
| 2007/0100297 A1 | 5/2007 | Woehr et al. | |
| 2007/0129689 A1 | 6/2007 | Woehr et al. | |
| 2007/0156093 A1 * | 7/2007 | Woehr | A61M 25/0618 604/164.08 |
| 2007/0179446 A1 | 8/2007 | Carrez et al. | |
| 2007/0179447 A1 | 8/2007 | Carrez et al. | |
| 2008/0097344 A1 | 4/2008 | McKinnon et al. | |
| 2008/0108944 A1 * | 5/2008 | Woehr | A61B 5/1411 604/164.08 |
| 2009/0281499 A1 * | 11/2009 | Harding | A61M 25/0618 604/164.08 |
| 2011/0160662 A1 * | 6/2011 | Stout | A61M 25/0097 604/122 |
| 2011/0319825 A1 * | 12/2011 | Goral | A61M 25/0097 604/164.01 |

FOREIGN PATENT DOCUMENTS

| | | |
|---|---|---|
| JP | 2012519057 | 8/2012 |
| WO | 01/23029 A1 | 4/2001 |
| WO | 02/45786 A2 | 6/2002 |
| WO | 2009/154824 A1 | 12/2009 |

* cited by examiner

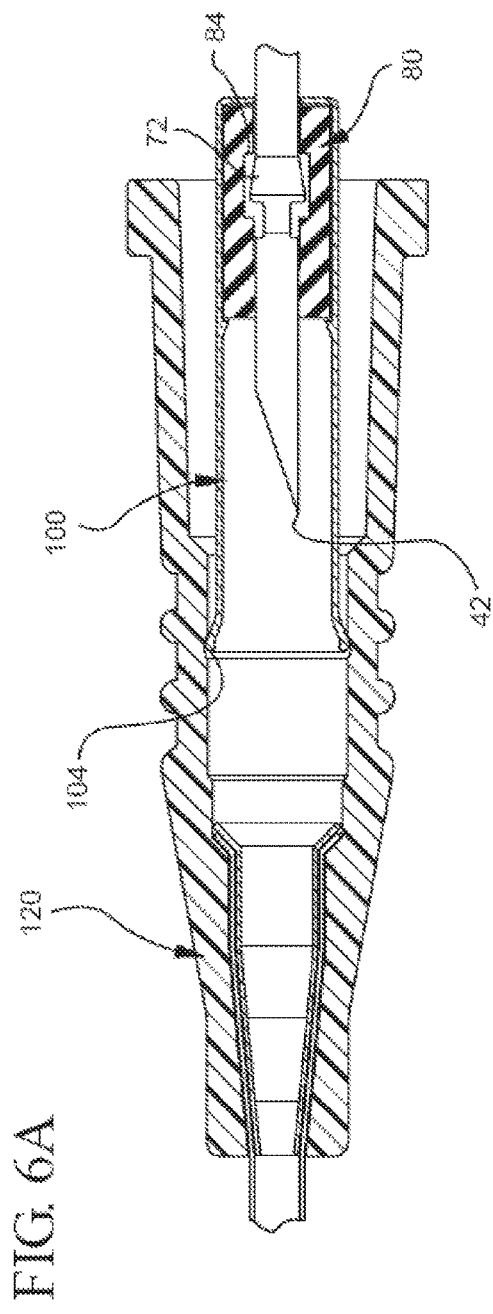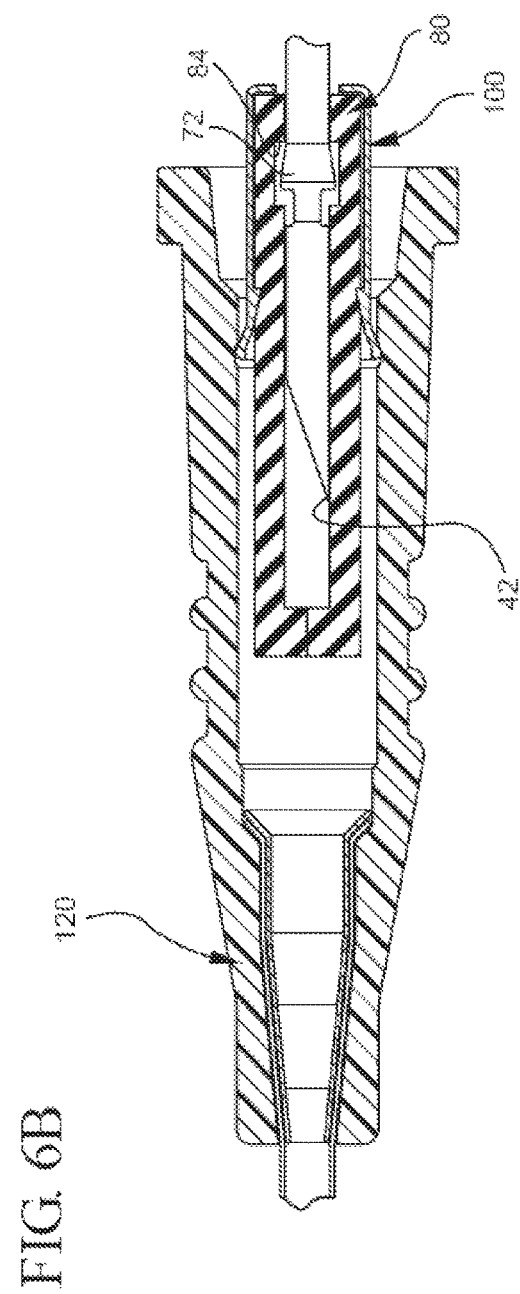
FIG. 6A
FIG. 6B

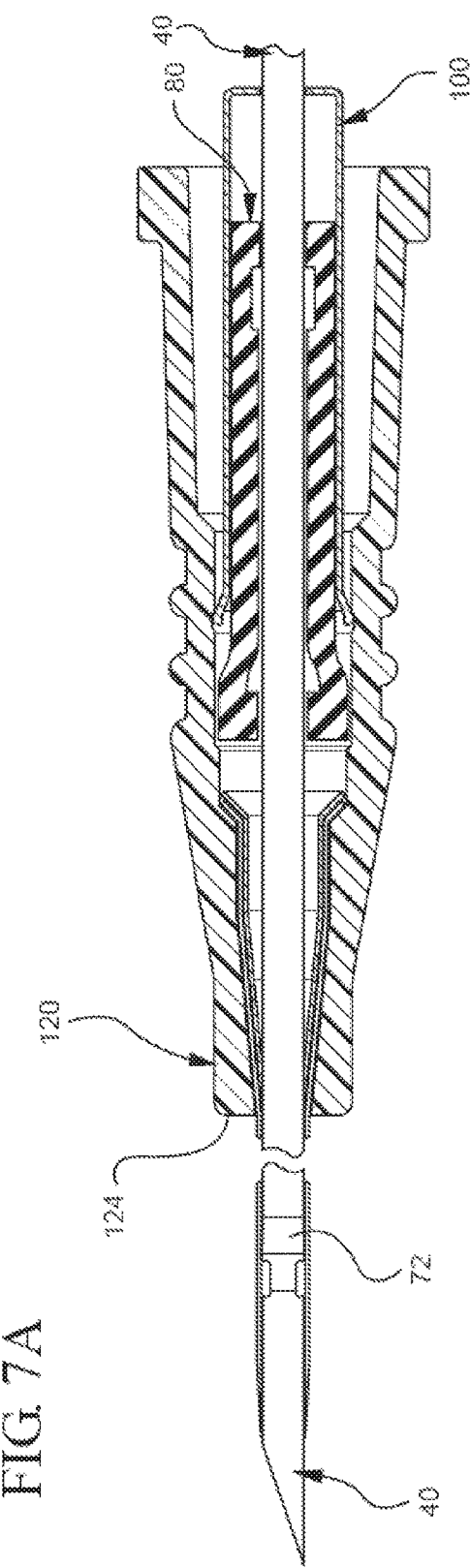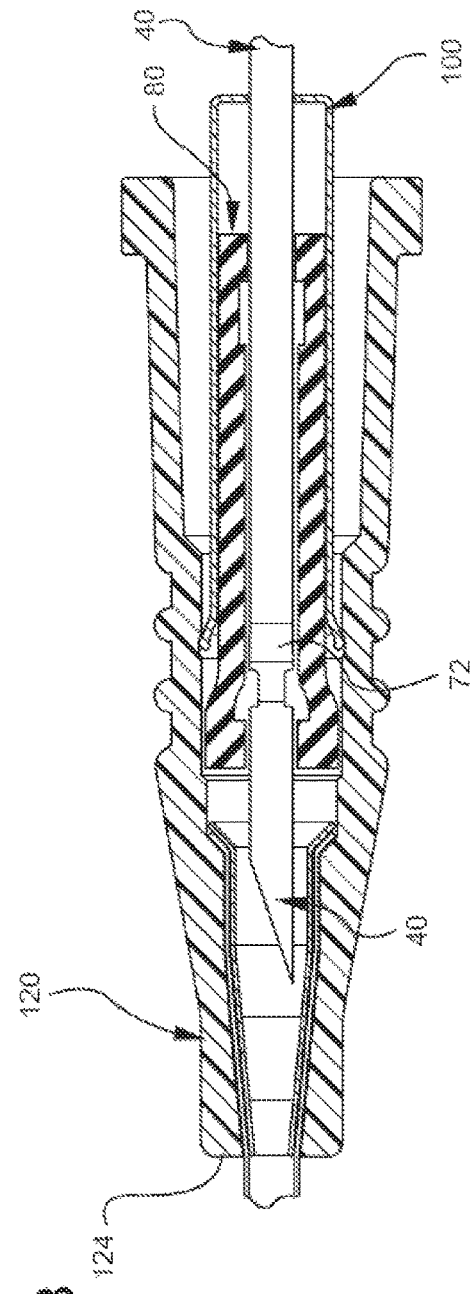

BI-DIRECTIONAL CANNULA FEATURE CAPTURE MECHANISM

CROSS-REFERENCE TO RELATED APPLICATIONS

This application is a continuation of U.S. patent application Ser. No. 13/939,575, filed Jul. 11, 2013, entitled BI-DIRECTIONAL CANNULA FEATURE CAPTURE MECHANISM which is a continuation-in-part of U.S. patent application Ser. No. 12/396,289, filed Mar. 2, 2009, entitled BI-DIRECTIONAL CANNULA FEATURE CAPTURE MECHANISM, and are incorporated herein by reference.

BACKGROUND OF THE INVENTION

This disclosure relates generally to vascular access devices and associated methods. More specifically, this disclosure discusses a bi-directional cannula feature capture mechanism that is adapted to capture a cannula feature in a manner that locks the cannula in a shielded position. The bi-directional cannula feature capture mechanism can be used with catheter assemblies.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly to help guide the needle and to facilitate its cooperation with the catheter. At least the inner surface of the distal portion of the catheter tightly engages the outer surface of the needle to prevent peelback of the catheter and, thereby, facilitate insertion of the catheter into the blood vessel. The catheter and the introducer needle are often assembled so that the distal tip of the introducer needle extends beyond the distal tip of the catheter. Moreover, the catheter and needle are often assembled so that, during insertion, the bevel of the needle faces up, away from the patient's skin. The catheter and introducer needle are generally inserted at a shallow angle through the patient's skin into a blood vessel.

In order to verify proper placement of the needle and/or catheter in the blood vessel, the operator generally confirms that there is "flashback" of blood into a flashback chamber associated with the needle assembly. Flashback generally entails the appearance of a small amount of blood, which is visible within the needle assembly or between the needle and the catheter. Once proper placement of the distal tip of the catheter into the blood vessel is confirmed, the operator may apply pressure to the blood vessel by pressing down on the patient's skin over the blood vessel, distal to the introducer needle and the catheter. This finger pressure momentarily occludes the vessel, minimizing further blood flow through the introducer needle and the catheter.

The operator may then withdraw the introducer needle from the catheter. The needle may be withdrawn into a needle tip cover or needle cover that extends over the needle's tip and prevents accidental needle sticks. In general, a needle tip cover includes a casing, sleeve, or other similar device that is designed to trap/capture the needle tip when the introducer needle is withdrawn from the catheter and the patient. After the needle is withdrawn, the catheter is left in place to provide intravenous access to the patient.

The separation of the introducer needle assembly from the catheter portions of the catheter assembly presents numerous potential hazards to the operators and others in the area. As indicated above, there is a risk of accidental needle sticks if the needle tip is not secured properly in a needle tip shield. Additionally, because the needle has been in contact with blood in the patient's vasculature, blood is often present on the needle's exterior as well as inside the lumen of the needle. As the needle is withdrawn from the catheter, there is a risk that this blood will drip from the needle tip or come into contact with other surfaces to expose people and equipment to blood. Additionally, it has been observed that withdrawing a needle from a catheter assembly often imparts energy to the parts of the needle assembly. For instance, during needle withdrawal, bending forces can be applied (either unintentionally or intentionally) to the needle. Such energy has been observed to cause blood to splatter or spray from the needle when the needle vibrates and shakes as it becomes free from the catheter assembly and releases the stored energy.

The present disclosure discusses a bi-directional cannula feature capture mechanism that allows a needle with a cannula feature to be retracted from an unshielded position to a shielded position in which the cannula feature is bi-directionally trapped. Accordingly, the described capture mechanism is configured to lock the needle in the shielded position to significantly limit or prevent accidental sticks and blood exposure after the needle is withdrawn from a catheter assembly.

BRIEF SUMMARY OF THE INVENTION

The present application relates to a bi-directional cannula feature capture mechanism that is designed to overcome some of the limitations known in the art. Typically, the capture mechanism comprises a cannula with a cannula feature, an inner housing, an outer housing, and a catheter adapter. In some cases, when the cannula is in an unshielded position, the inner housing is received in the outer housing in a manner that allows the inner housing to translate proximally through the outer housing. The cannula also extends axially through the inner housing and the outer housing so that the cannula's distal tip extends past the distal ends of both the inner and the outer housing. Additionally, in the unshielded position, a distal portion of the cannula optionally extends into a catheter and the outer housing is optionally coupled to a catheter adapter.

In some cases, when a proximal force retracts the cannula into a shielded position, the cannula translates proximally into the inner housing until a feature on the cannula becomes bi-directionally engaged by the inner housing. In other words, the cannula feature moves proximally into the inner housing until the feature becomes trapped in a manner that restricts the cannula's proximal and distal movement and irreversibly locks the cannula in the shielded position.

As the proximal force on the cannula continues, the frictional force experienced between the cannula and the inner housing becomes greater than the frictional force experienced between the inner housing and the outer housing. As a result, the inner housing translates proximally through and becomes trapped in the outer housing. Once the cannula feature is trapped by the inner housing and the inner housing is trapped by the outer housing so the cannula is shielded, the outer housing may uncouple from the catheter adapter so the catheter can be used and the cannula/capture mechanism can be safely disposed.

The cannula may comprise any cannula that can be used with the described capture mechanism, including, but not limited to, a hypodermic needle, such as an IV catheter introducer needle. Additionally, the cannula may comprise any component or characteristic that allows it to be used with, and be captured by, the described capture mechanism. In one example, the cannula comprises a bi-directionally engageable cannula feature, such as a notched crimp feature, a welded ferrule feature, a notch feature, a crimp feature, or another cannula feature that has an outer diameter ("OD") that extends laterally past the OD of the cannula. In this example, the cannula feature comprises a proximal engagement and a distal engagement, which are adapted to contact corresponding surfaces in the inner housing to respectively restrict the cannula feature's proximal and distal movement in the housing.

The inner housing may comprise any component or characteristic that allows it to bi-directionally capture the cannula feature in a manner that limits the proximal and distal movement of the cannula when the cannula is in a shielded position. In one example, the inner housing comprises an interior space through which the cannula extends axially. In another example, the inner housing comprises a proximal cannula feature mating component that is adapted to contact the feature's proximal engagement and stop the feature's proximal movement in the housing. In still another example, inner housing comprises a distal cannula feature mating component that is adapted to contact the cannula feature's distal engagement and stop the feature's distal movement after the feature has moved proximally past the distal mating component.

The outer housing may comprise a variety of suitable components or characteristics that allow the inner housing to slide proximally into the outer housing. In some instances, the outer housing comprises a canister or a ring that is sized and shaped to receive the inner housing. The outer housing can also be configured to be locked to the inner housing in a manner that prevents the inner housing from sliding distally with respect to the outer housing when the cannula feature is captured by the proximal and distal mating components. For example, the outer housing may comprise a catch and corresponding interlock surface, a one-directional barb, or another retention feature that prevents the inner housing from moving distally in the outer housing, once the feature has become bi-directionally captured.

The outer housing can be configured to selectively and removably couple to any suitable catheter adapter, in any suitable manner. For example, the outer housing may comprise an interlock component that is biased against a corresponding adapter interlock surface of the adapter when the cannula is in an unshielded position. In this example, the interlock component is relaxed when the cannula is moved to a shielded position. Accordingly, the shielded cannula can be uncoupled from the catheter adapter and unintentional sticks can be prevented.

BRIEF DESCRIPTION OF THE SEVERAL VIEWS OF THE FIGURES

In order that the manner in which the above-recited and other features and advantages of the invention will be readily understood, a more particular description of the bi-directional cannula feature capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which:

FIGS. 5A, 5B, 6A, and 6B each illustrate a partial cut-away plan view of a different embodiment of the bi-directional cannula feature capture mechanism in which the cannula is in the shielded position;

FIGS. 7A, 7B, 7C, 7D, and 7E illustrate a partial cut-away plan or perspective view of a representative embodiment of a method for using the bi-directional cannula feature capture mechanism;

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the bi-directional cannula feature capture mechanism, as represented in FIGS. 1 through 7E, is not intended to limit the scope of the invention, as claimed, but is merely representative of some presently preferred embodiments of the invention.

Generally, this application relates to a bi-directional cannula feature capture mechanism. In other words, this application discusses a cannula feature capture mechanism that allows a cannula with a feature to be moved from an unshielded position to a shielded position in which the cannula feature is trapped and prevented from moving proximally and distally out of the capture mechanism. As used herein, the term "unshielded" may refer to circumstances in which the cannula's distal tip is exposed from the capture mechanism. Conversely, the term "shielded" may refer to circumstances in which the cannula's tip is covered, shielded, or otherwise protected. Because the capture mechanism allows the cannula to be locked in the shielded position, the capture mechanism may prevent unintended sticking and/or blood exposure. To better explain the capture mechanism, a more detailed description of the mechanism is given below, followed by a more detailed description of the mechanism's use.

Figure 1:
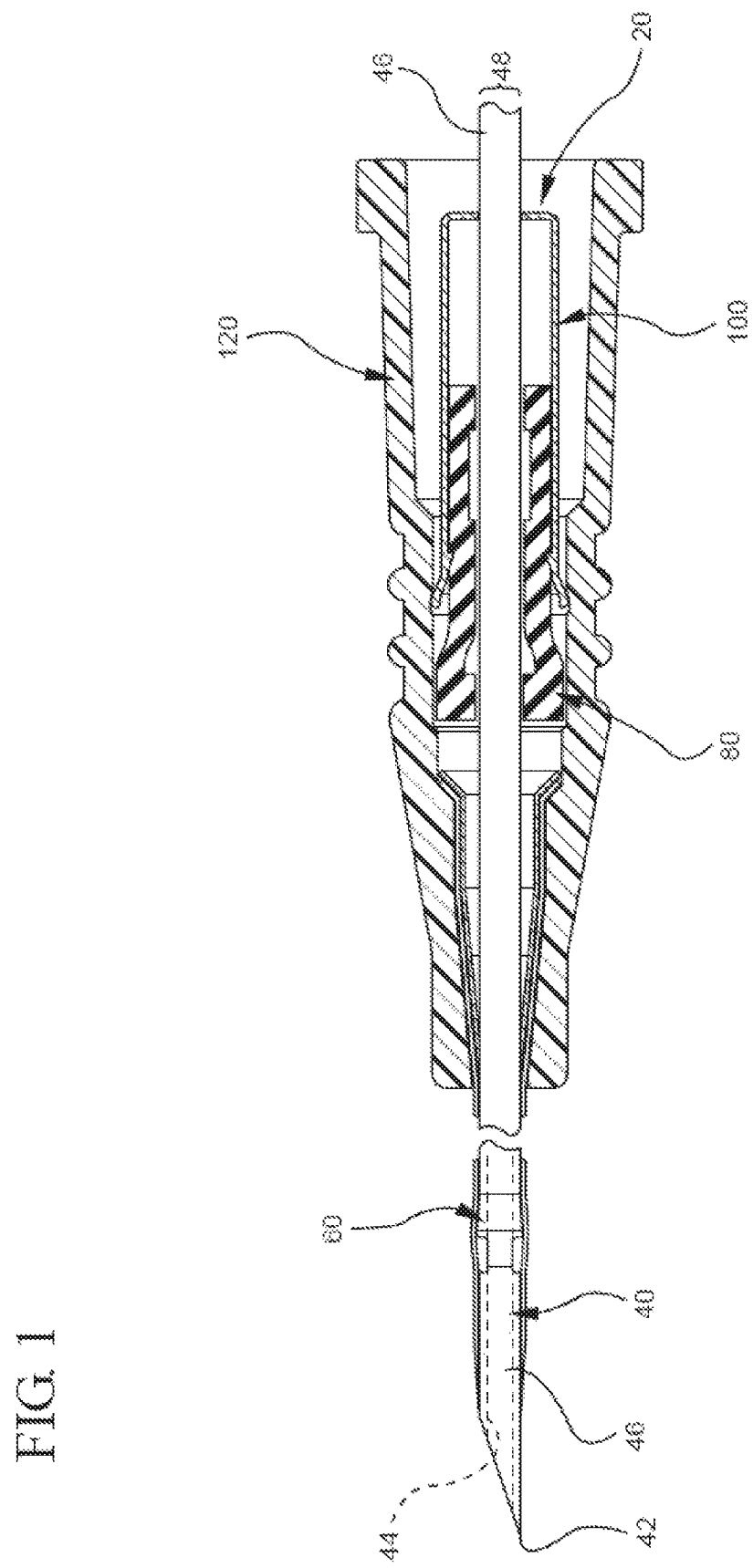
FIG. 1 illustrates a partial cut-away plan view of a representative embodiment of a catheter adapter comprising a bi-directional cannula feature capture mechanism in which a catheter is disposed in an unshielded position.

The capture mechanism can comprise any component or characteristic that allows it to bi-directionally capture a cannula feature when the cannula is in the shielded position. For example, FIG. 1 shows a representative embodiment in which the bi-directional cannula feature capture mechanism 20 comprises a cannula (e.g., needle 40), a bi-directionally engageable cannula feature (e.g., needle feature 60), an inner housing 80, and an outer housing 100. Additionally, FIG. 1 shows that the capture mechanism 20 can selectively be coupled with a catheter adapter 120. To provide a better understanding of the capture mechanism 20, each of the aforementioned components is described in below in further detail.

FIG. 1 shows the capture mechanism 20 comprises a cannula (e.g., needle 40). As used herein, the terms "cannula" and "cannulae" may refer to virtually any rigid tube that is configured to be inserted into an animal's body to draw off or to introduce fluid, wherein the tube comprises a sharpened tip that allows the tube to puncture the body and access an intended space. Some examples of such cannulae comprise hypodermic needles and other cannulae that may expose their operator to the risk of unintended sticking or blood exposure.

Where the cannula comprises a hypodermic needle, the cannula may comprise any suitable type of hypodermic needle, including an introducer needle for use in an IV catheter assembly (e.g., an over-the-needle peripheral IV catheter assembly). Indeed, according to some presently preferred embodiments, FIG. 1 shows the cannula comprises an introducer needle 40.

The introducer needle may have any characteristic that is suitable for use with an IV catheter assembly. By way of illustration, FIG. 1 shows an embodiment in which the introducer needle 40 comprises a sharpened distal tip 42, a lumen 44 (not directly shown), an elongated tubular portion 46 with a substantially constant outer diameter ("OD") 48, and a bi-directionally engageable needle feature 60. Additionally, each of the needle's aforementioned components may comprise any suitable characteristic. For example, the distal tip of the needle may comprise a standard bevel, a short bevel, a true short bevel, a bias grind point, a vet point, a lancet point, a deflected point (anti-coring), or another suitable needle point. In another example, the lumen and elongated tubular portion may be any suitable size. For instance, the needle may be any length or gauge (e.g., from a 7 to a 33 on the Stubs scale) that allows it to be used as the introducer needle in an IV assembly.

Figure 2A:
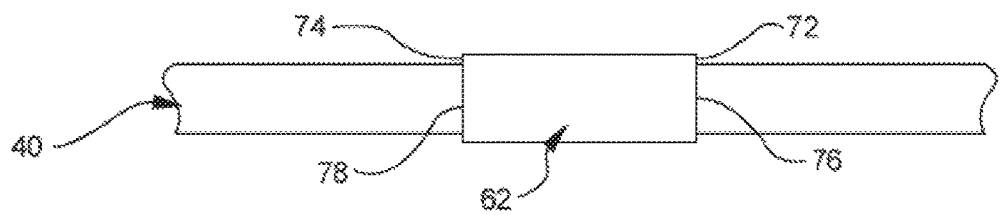
FIGS. 2A-2E each illustrate a plan or perspective view of a representative embodiment of a suitable cannula feature.
Figure 2B:
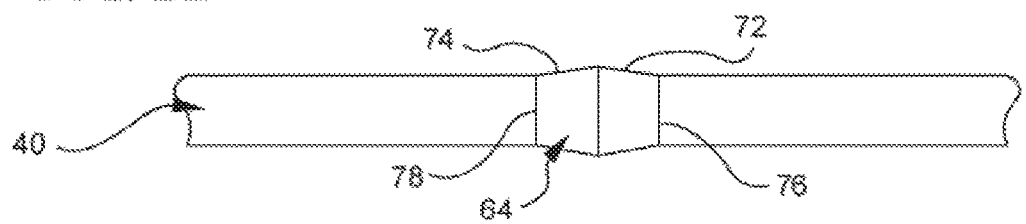
Figure 2C:
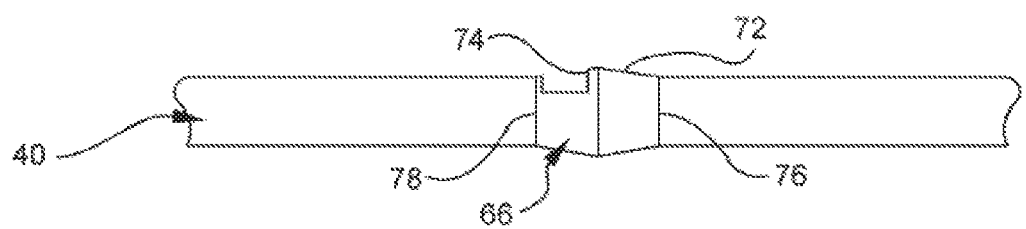
Figure 2D:
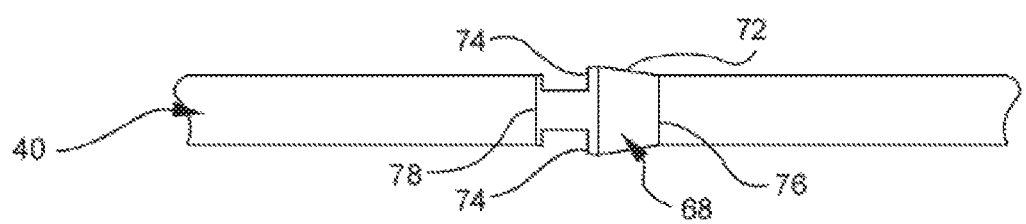
Figure 2E:
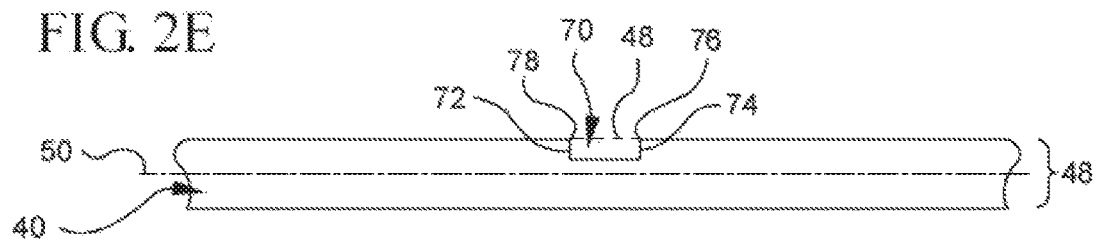

Regarding the bi-directional needle feature, the needle may comprise any needle feature that is capable of being captured in the inner housing (as described below) in a manner that restricts the feature's distal and proximal movement within the inner housing. For instance, the feature may comprise any suitable needle feature that has an OD that is greater than the needle's OD or has at least one surface that extends laterally past the needle's OD. Indeed, in some embodiments, the feature comprises one or more one-way barbs. Similarly, FIG. 2A shows that, in at least one embodiment, the feature comprises a welded ferrule 62. FIG. 2B shows that, in another representative embodiment, the feature comprises a crimp feature 64. FIGS. 2C and 2D show that, in still other embodiments, the feature comprises a crimp with a single notch 66 and a plurality of notches 68, respectively. However, FIG. 2E shows that in at least one other embodiment, the feature comprises a notch 70.

Regardless of the specific type of needle feature, the feature may have any suitable characteristic. For instance, the feature may be any suitable shape or size. Similarly, the feature may include any suitable component that allows the needle to function as intended and become bi-directionally engaged when the needle is retracted to the shielded position. For instance, FIGS. 2A through 2E show that the various needle features (e.g., 62, 64, 66, 68, and 70) comprise a proximal engagement 72 and a distal engagement 74.

The needle feature's proximal engagement may have any suitable characteristic that allows the feature to be prevented from moving proximally out of the inner housing. For example, FIGS. 2A-2D show some embodiments in which a proximal side 76 of the features 62, 64, 66, and 68 comprises a surface (e.g., proximal engagement 72) that extends past the needle's OD 48. In contrast, FIG. 2E shows a representative embodiment in which the proximal engagement 72 comprises a surface that extends from the needle's OD 48 towards a longitudinal axis 50 of the needle 40, at a distal side 78 of the notch feature 70.

The needle feature's distal engagement may also have any suitable characteristic that allows the feature to be prevented from moving distally out of the inner housing, once the needle has been moved into the shielded position. For example, FIGS. 2A-2D show some embodiments in which a distal side 78 of the features 62, 64, 66, and 68 comprises a surface 74 that extends laterally past the needle's OD 48. On the other hand, FIG. 2E illustrates a representative embodiment in which the distal engagement 74 comprises a surface that extends axially from the needle's OD 48, towards the needle's longitudinal axis 50, and at the proximal side 76 of the notch feature 70.

In some presently preferred embodiments, the needle feature comprises notched crimp feature (e.g., notched crimp feature 66 or 68). Indeed, such a feature may offer several advantageous characteristics. For instance, in addition to providing a surface that acts as the needle's distal engagement, the notch in the notched crimp feature may also serve other suitable purposes. For example, the notch may allow an operator to see "flashback" when the catheter is placed in a patient's blood vessel. For instance, where the needle is placed within another device (e.g., a catheter) and the needle is inserted into a patient's vasculature, blood flows through the needle's lumen, exits the lumen through the notch, and travels between the outer diameter of the lumen and the inner diameter of the other device (e.g., a catheter). Accordingly, where the other device is at least partially transparent, an operator may visualize a small amount of blood and, thereby, confirm placement of the catheter within the patient's blood vessel. For a more detailed description of suitable notched crimp features and the advantages, see U.S. patent application Ser. No. 12/396,227, entitled Bi-directionally Engageable Cannula Crimp Feature, filed Mar. 2, 2009, the entire disclosure of which is hereby incorporated by reference.

Figure 3A:
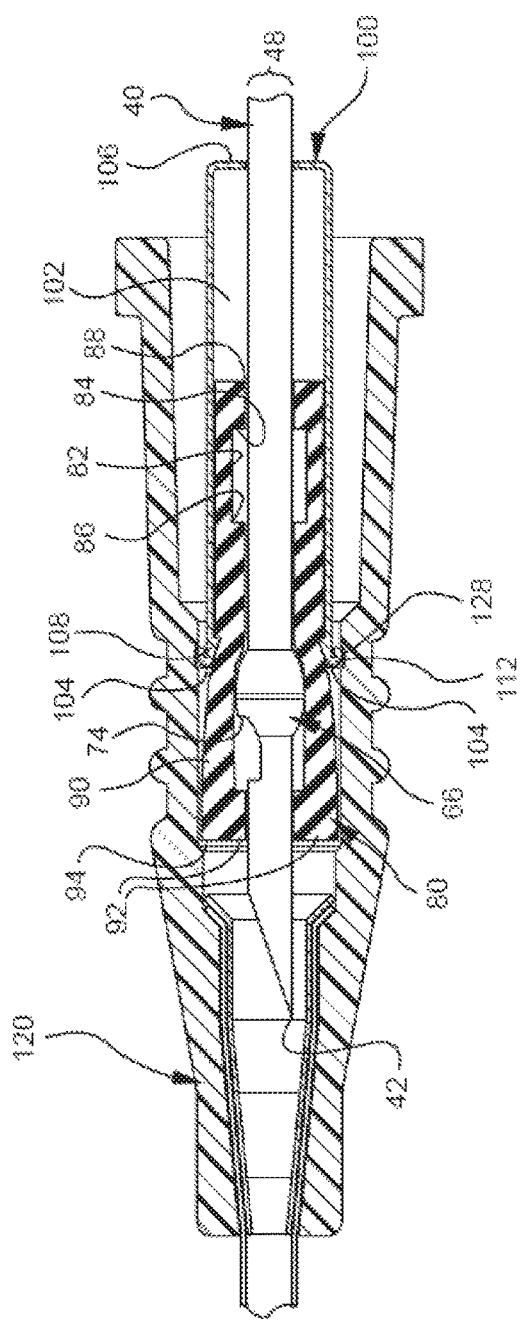
FIG. 3A illustrates a partial cut-away plan view of a representative embodiment of the bi-directional cannula feature capture mechanism in which the cannula tip is in the unshielded position.

As previously mentioned, the capture mechanism also comprises an inner housing. The inner housing may comprise any suitable characteristic that both allows it to move proximally in the outer housing and allows the needle feature to be retracted proximally until it becomes bi-directionally engaged. In one example of a suitable characteristic, the inner housing may be any suitable size or have any suitable shape through which the needle may axially pass. For instance, the inner housing can be substantially cylindrical, cuboidal, tubular, etc. Indeed, FIG. 3A shows a cut-away view of a representative embodiment in which the inner housing 80 has a substantially cylindrical shape. In another example of a suitable characteristic, the inner housing comprises a collet style housing that biases towards the needle as the inner housing translates proximally through the outer housing. By way of illustration, FIG. 3A shows an embodiment in which the inner housing 80 comprises a splayed housing that is split longitudinally down at least one side.

The inner housing may also have any suitable component that allows it to bi-directionally engage the needle feature once the needle as been retracted to the shielded position. For example, FIG. 3A shows the inner housing 80 comprises inner walls 82, which define an interior space 84 through which the needle 40 axially extends. In another example, FIG. 3A shows the inner housing 80 comprises a proximal needle feature mating component ("proximal mating component") 84 and a distal needle feature mating component ("distal mating component") 86.

The proximal mating component may comprise any suitable surface that is configured to contact needle feature's proximal engagement and prevent the feature from being proximally extracted out of the inner housing. For instance, the proximal mating component may comprise a needle port, one or more surfaces that extend axially from the inner walls, one or more one-way barbs, or another surface that is adapted to contact the feature's proximal engagement and prevent the feature from moving proximally past the surface. In one example, FIG. 3A shows the proximal mating component 84 comprises a needle port 88 that is sized and shaped to allow the needle 40, but not the notched crimp feature 66 with its surfaces that extend laterally past the needle's OD (e.g., the proximal engagement 72), to pass therethrough. While FIG. 3A shows needle port 88 may limit the proximal movement of the notched crimp feature 66 relative to the inner housing 80, such a proximal mating component 84 may also act to limit the proximal movement of other needle feature's having laterally extending surfaces (e.g., features 62, 64, and 68 from FIG. 2).

Where the proximal mating component comprises a needle port, the port may have any suitable characteristic. For instance, the needle port may be configured to wipe or squeegee fluids (e.g., blood) from the OD of the needle as the needle is pulled proximally through the needle port. This squeegee effect may be provided in any suitable manner. For example, the port may comprise a rubber, plastic, elastomeric, or other similar ring that is capable of wiping blood from the needle. Accordingly, the inner housing may further reduce the risk of blood exposure.

In another example of a suitable proximal mating component (not shown), the proximal mating component comprises a surface that extends axially from the inner housing's inner walls (e.g., wall 82) and is configured to extend towards the longitudinal axis of the needle. For instance, the proximal mating component may comprise a protuberance that is adapted to extend into a notch feature (e.g., notch feature 70 in FIG. 2E). In such instances, when the needle is moved to the shielded position, a distal side of the protuberance is adjacent to the notch's proximal engagement, so that when proximal force is applied to the needle, the protuberance's distal side contacts the proximal engagement to prevent the engagement from moving proximally respective to the inner housing.

The distal mating component may comprise any suitable surface that is configured to contact the needle feature's distal engagement and limit the feature's distal movement respective to the inner housing after the needle has been moved to the shielded position. For instance, the distal mating component may comprise one or more one-way barbs, one or more surfaces that extend axially from the inner housing's inner walls, and/or another surface that is adapted to contact the feature's distal engagement and prevent the feature from moving distally after the needle has been moved to the shielded position.

Figure 3B:
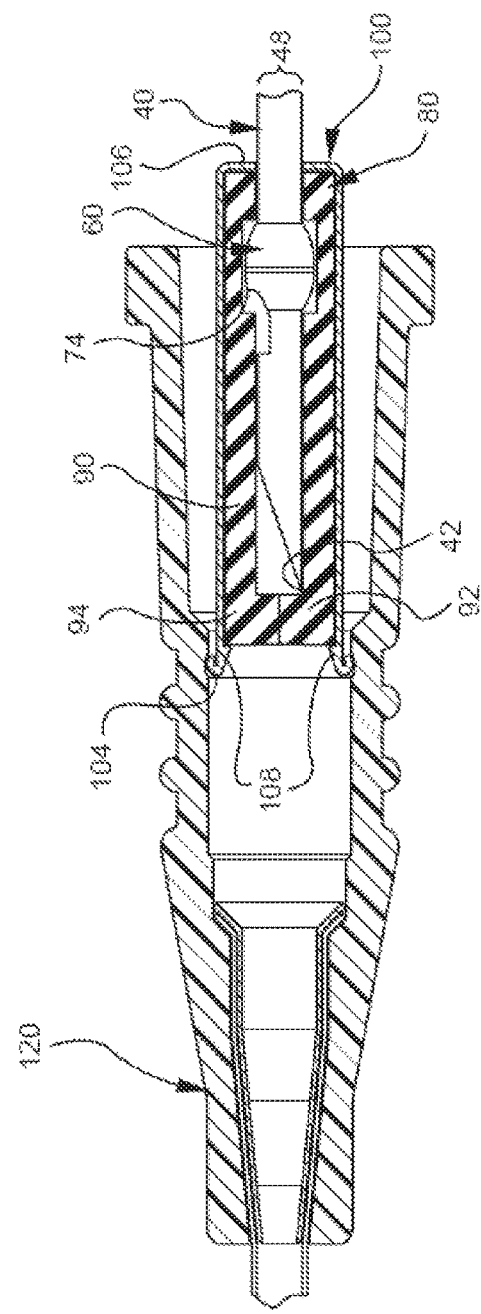
FIG. 3B illustrates a partial cut-away plan view of a representative embodiment of the bi-directional cannula feature capture mechanism in which the cannula tip is in a shielded position.

In one example, FIG. 3A shows the distal mating component 86 comprises a surface that extends axially from the inner wall 82 towards the needle 40. In this example, once the distal engagement 74 translates proximally past the distal mating component 86, the distal mating component is biased towards the needle's OD 48, as shown in FIG. 3B. Accordingly, the distal mating component 86 moves into a position that blocks the feature's distal engagement 74 from moving distally when a distal force is applied to the needle 40. While FIG. 3B shows the distal mating component 86 is configured to mate with a notched crimp feature 66, such a distal mating component 86 may also be used or modified to prevent the distal movement of other features comprising a surface that extends laterally past the needle's OD (e.g., needle features 62, 64, and 68).

In another example of a suitable distal mating component (not shown), the distal mating component comprises a surface (e.g., a protuberance) that extends axially from the inner housing's inner walls and is configured to extend into a notch feature (e.g., feature 70 in FIG. 2E) when the needle is in the shielded position. In this example, when the needle is in the shielded position, a proximal side of the protuberance is adjacent to the notch's distal engagement (e.g., 74). Thus, when distal force is applied to the needle, the protuberance's proximal side contacts the distal engagement and prevents the engagement from moving distally respective to the inner housing.

In addition to the previously mentioned components, the inner housing may have any other suitable component that allows it to bi-directionally capture the needle's feature and be used with a catheter assembly. For instance, the inner housing may comprise any suitable type of needle shielding component. By way of example, FIG. 3B shows the inner housing 80 comprises needle shields 90 that extend distally past the distal mating component 86. While the needle shields 90 may have any characteristic that allows them to cover the needle 40 and protect people from unintentional sticking, FIG. 3B shows a representative embodiment in which the needle shields 90 are long enough to extend past the needle's distal tip 42. Additionally, FIG. 3B shows the needle shields 90 optionally comprise transverse barriers 92 that provide a needle tip capture mechanism that acts as a redundant needle capture mechanism and further encloses the needle tip 42 to reduce the risk of blood exposure.

As previously mentioned, the capture mechanism comprises an outer housing that is configured to receive the inner housing and allow the inner housing to translate proximally in the outer housing until reaching an inner housing stop. The outer housing may have any suitable characteristic that allows the capture mechanism to operate as intended. In one example, FIG. 3A shows the outer housing 100 has an interior space 102 that is sized and shaped to receive the inner housing 80 in a manner that biases the distal end 104 of the outer housing 100 away the needle 40 when the needle 40 is in the unshielded position. In another example, FIG. 3B shows the outer housing 100 is sized and shaped to receive the inner housing 80 in a manner that biases the inner housing 80 towards the needle 40 when the needle 40 is in the shielded position and the inner housing 80 has been moved proximally towards an inner housing stop 106. As used herein, the term "inner housing stop" may refer to any suitable surface of the outer housing that is adapted to limit the inner housing's proximal movement with respect to the outer housing.

In still another example of a suitable characteristic of the outer housing, the outer housing may be configured so that the friction force experienced between the inner housing and the outer housing is greater than the friction force experienced between the inner housing and the needle until the needle's feature is captured by the distal and proximal mating component. In this example, when the needle is in the unshielded position and a proximal force is applied to it, the needle is allowed to translate proximally into the inner housing without causing the inner housing to translate proximally into the outer housing. However, once the feature's proximal engagement contacts the proximal mating component, the frictional force between the needle and the inner housing is greater than the frictional force experienced between the inner housing and the outer housing. Accordingly, as the proximal force continues to be applied to the needle, the inner housing is caused to translate proximally into the outer housing.

In some embodiments, the outer housing (and/or the inner housing) comprises means for locking the inner housing to the outer housing when the needle is in the shielded position. In such embodiments, the locking means can comprise any suitable component or characteristic that allows the inner housing to translate proximally into the outer housing but not to reemerge distally. For instance, the outer housing and/or the inner housing may include one or more one-way barbs, catches and corresponding interlock surfaces, or other retention components that are capable of locking the inner housing to the outer housing when the needled is in the shielded position.

Figure 4:
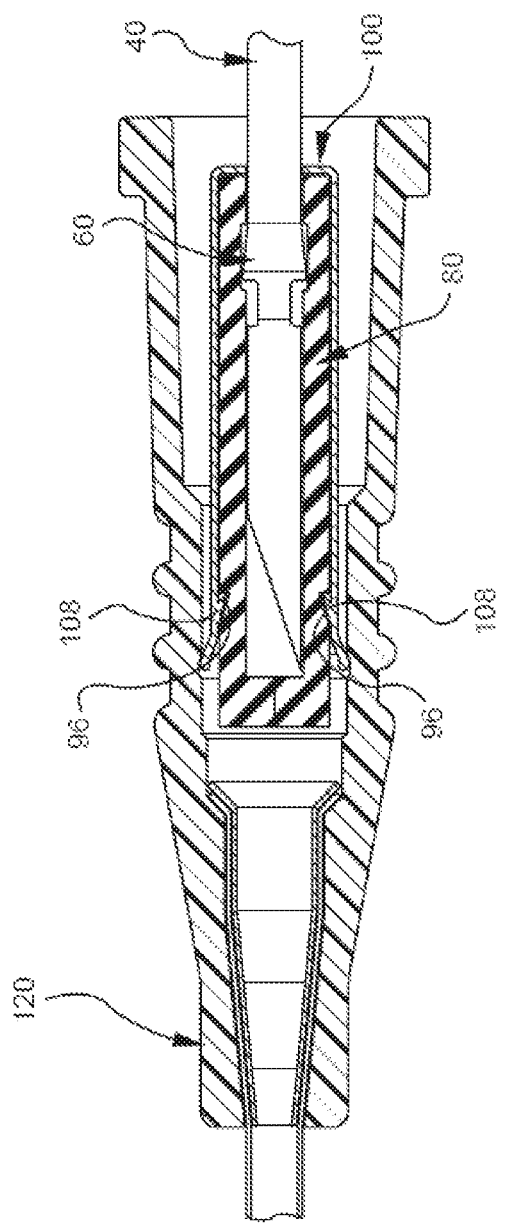
FIG. 4 illustrates a plan view of a portion of a partial cut-away view of a representative embodiment of the bi-directional cannula feature capture mechanism in which the cannula is in the shielded position.
Figure 5A:
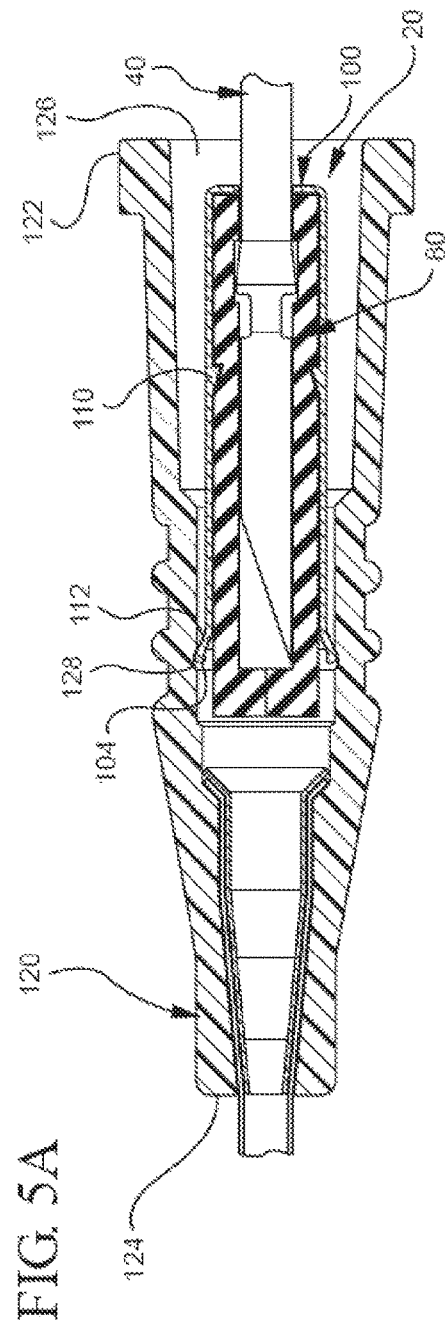

By way of example, FIG. 3B shows an embodiment in which the distal end 104 of the outer housing 100 comprises a plurality of catches 108 that act as locking means and seat against the distal end 94 of the inner housing 80 to lock the inner housing 80 in place when the needle 40 is in the shielded position. In another example, FIG. 4 shows a representative embodiment in which the outer housing 100 comprises plurality of catches 108 that are adapted to mate with corresponding interlock surfaces 96 in the inner housing 80 when the needle 40 is in the shielded position. In still another example, FIG. 5A shows a representative embodiment in which the outer housing 100 comprises a plurality of one-way barbs 110 that gouge into the inner housing 80 and prevent it from translating distally through the outer housing 100 once the needle 40 is shielded.

Where the outer housing is made of a material with a different level of flexibility than the inner housing, the differing flexibilities may further help keep the two housings locked together after the needle has been shielded. Thus, in some embodiments, the inner housing and the outer housing each comprise a material with a different level of flexibility. In one example, the outer housing comprises a first material that is less flexible than a second material of the inner housing. For instance, the outer housing comprises a first material (e.g., a metal, a metal alloy, a ceramic, a hardened polymer etc.), while the inner housing comprises a more flexible material (e.g., a plastic, a polymer, etc.). In this example, the inner housing may resiliently flex around catches, barbs, and/or other retention features in the outer housing as the inner housing moves proximally relative to the outer housing. Additionally, in this example, the outer housing rigidly supports the inner housing after the inner housing has been moved proximally into the outer housing.

In another example, however, the outer housing comprises a first material that is more flexible than the second material of the inner housing. For example, the outer housing may comprise a plastic while the inner housing comprises a metal. In this example, the outer housing may resiliently flex as the inner housing translates distally through the outer housing.

In some embodiments, the distal mating component and the distal engagement are configured so that once the needle is moved into the shielded position, a distal force on the needle causes the distal engagement to press against the distal mating component in a manner that causes the inner housing to expand radially. This radial expansion, in turn, causes the inner housing to further bind in the outer housing and prevents the inner housing from moving distally with respect to the outer housing. This radial expansion can be accomplished in any suitable manner. For example, the feature's distal engagement (e.g., 74) and/or the inner housing's distal mating component (e.g., 86) may be sloped or otherwise configured to cause the inner housing to radially expand within the outer housing when a distal force is applied to the needle.

Figure 5B:
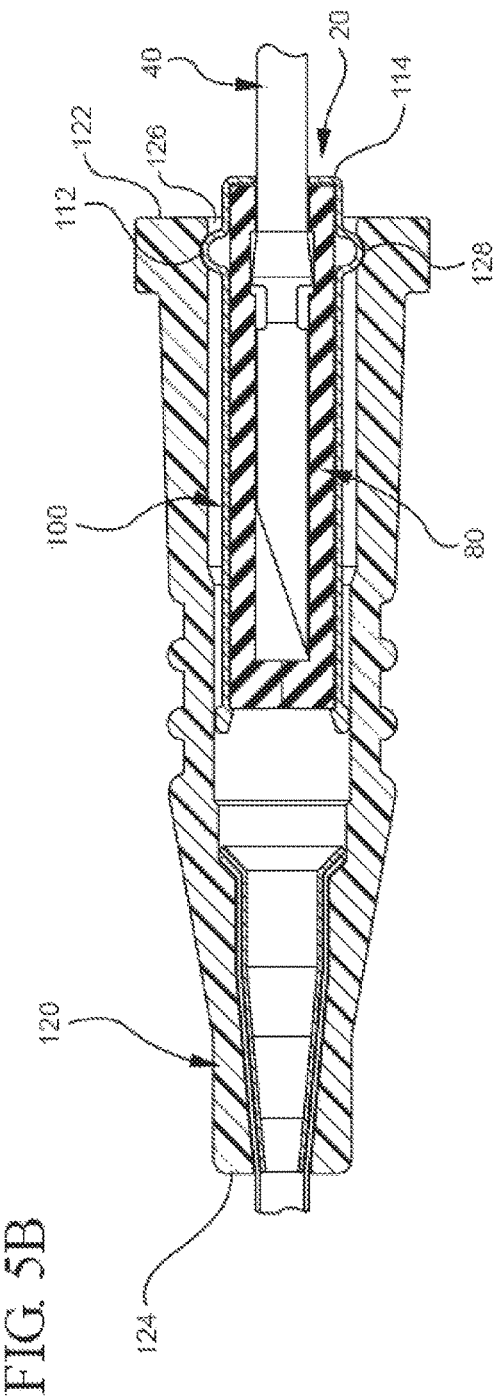

As mentioned above, in some embodiments, the capture mechanism is used with a catheter adapter. Indeed, the capture mechanism may be used with any suitable catheter adapter. Generally, FIG. 5A shows the catheter adapter 120 comprises a proximal end 122 and a distal end 124 with a lumen 126 extending between the two. FIG. 5A also shows that the proximal end 122 of the adapter 120 is configured to receive the capture mechanism 20 so the outer housing 100 can be coupled within the adapter's lumen 126. Although not shown in FIG. 5A, the skilled artisan will recognize that the adapter's distal end 124 can comprise a catheter with an inner diameter that is slightly larger than the outer diameter of the needle 40. Accordingly, in the unshielded position, the needle's tip 42 can extend distally past the adapter's distal end 124.

Where the capture mechanism is used in conjunction with a catheter adapter, the two can be coupled in any suitable manner that allows the capture mechanism to be coupled to the adapter when the needle is in the unshielded position and to be uncoupled from the adapter when the needle is in the shielded position. In one example of a suitable coupling mechanism, the outer housing comprises an interlock component that mates with a corresponding adapter interlock surface in the lumen of the adapter. In another example of a coupling mechanism, however, the outer housing comprises an adapter interlock surface that corresponds with an interlock component disposed within the adapter lumen.

Where the outer housing is selectively coupled within the catheter adapter by a coupling mechanism, the coupling mechanism may be located in any suitable position. For example, FIG. 5A shows a representative embodiment in which the adapter interlock surface 128 is located distally within the adapter's lumen 126. Furthermore, FIG. 5A shows the distal end 104 of the outer housing 100 is flared, bent, or otherwise comprises interlock component 112 that is suitable to mate with the interlock surface 128. In another example, however, FIG. 5B shows a representative embodiment in which the adapter interlock surface 128 is disposed proximally within the lumen 126 and the corresponding interlock component 112 is disposed near a proximal end 114 of the outer housing 100.

Where the outer housing is selectively coupled to the inner housing with a coupling mechanism comprising an interlock component and a corresponding adapter interlock surface, the coupling mechanism may function in any suitable manner. In one example, when the needle is in the unshielded position, the inner housing is splayed open in a manner that applies pressure to the distal end of the outer housing. In this example, the pressure from the inner housing causes interlock components (e.g., 112) at the distal end of the outer housing to be biased against corresponding interlock surfaces (e.g., 128) within the adapter's lumen. In another example, FIG. 5A shows that when the needle 40 is moved to the shielded position and the inner housing 80 is moved proximally into the outer housing 100, the interlock components 112 at the distal end 104 of the outer housing 100 are relaxed so the capture mechanism 20 with the shielded needle 40 can be safely uncoupled from the adapter 120.

In another example of how the coupling mechanism may work, the coupling mechanism may be configured so that the frictional force experienced between the interlock component and the adapter interlock surface is greater than the frictional force experienced between the inner housing and the outer housing and between the needle and the inner housing until the needle has been moved to the shielded position and the inner housing has moved adjacent to the inner housing stop. Accordingly, once the needle's feature has become bi-directionally engaged within the inner housing and the inner housing has become locked with the outer housing, additional proximal force, above the frictional force experienced between the interlock component and the adapter interlock surface, will cause the capture mechanism and shielded needle to become uncoupled from the adapter.

Figure 8:
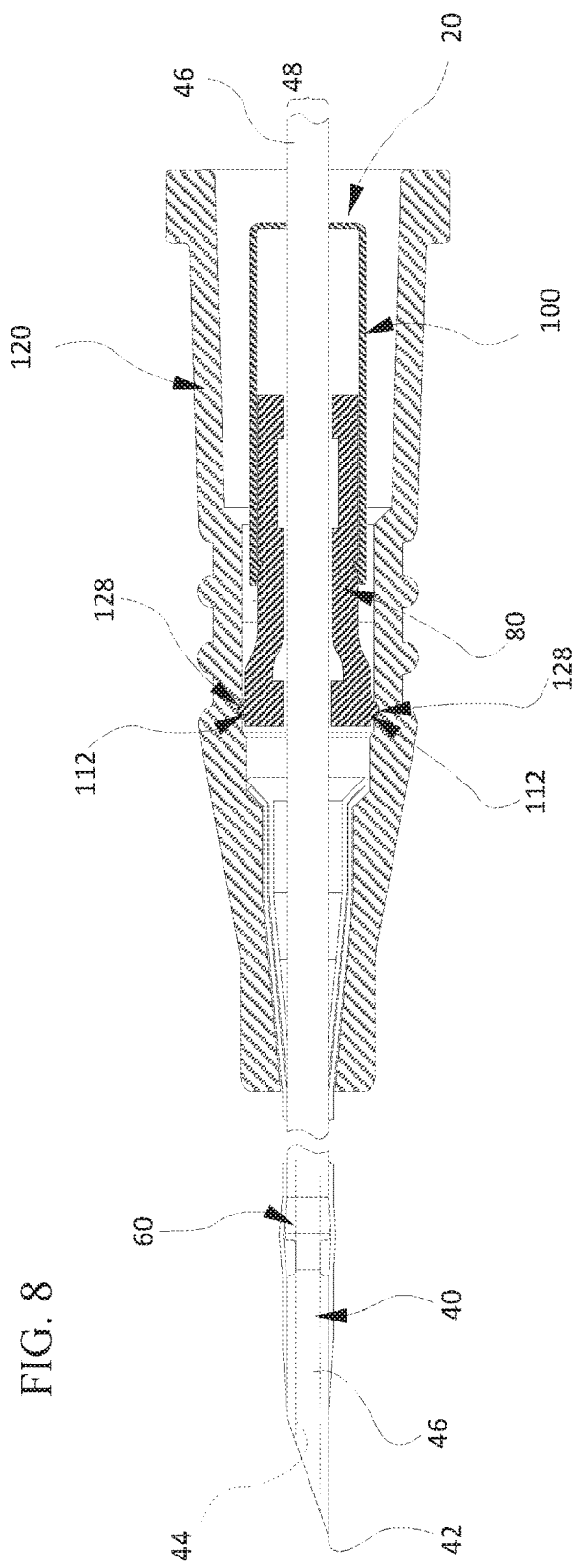
FIG. 8 illustrates a partial cut-away plan view of a representative embodiment of a catheter adapter in which interlock components are formed on the inner housing of the bi-directional cannula feature capture mechanism.

FIG. 8 illustrates an example where the interlock components 112 are formed on the inner housing 80 rather than the outer housing 100. In such cases, the interlock components 112 can be formed at any position of the outer surface of the inner housing 80 that is exposed to the inner surface of the adapter's lumen prior to the needle being shielded. Similarly, the interlock surfaces 128 can be formed in an appropriate location within the adapter's lumen so that when the interlock components 112 are inserted into the interlock surfaces 128, the capture mechanism is appropriately positioned within the lumen. Then, when the needle 40 is retracted into the inner housing 80, the distal end of the inner housing 80 contracts radially inward causing the interlock components 112 to separate from the interlock surfaces 128 thereby freeing the capture mechanism to be uncoupled from the adapter.

Figure 9:
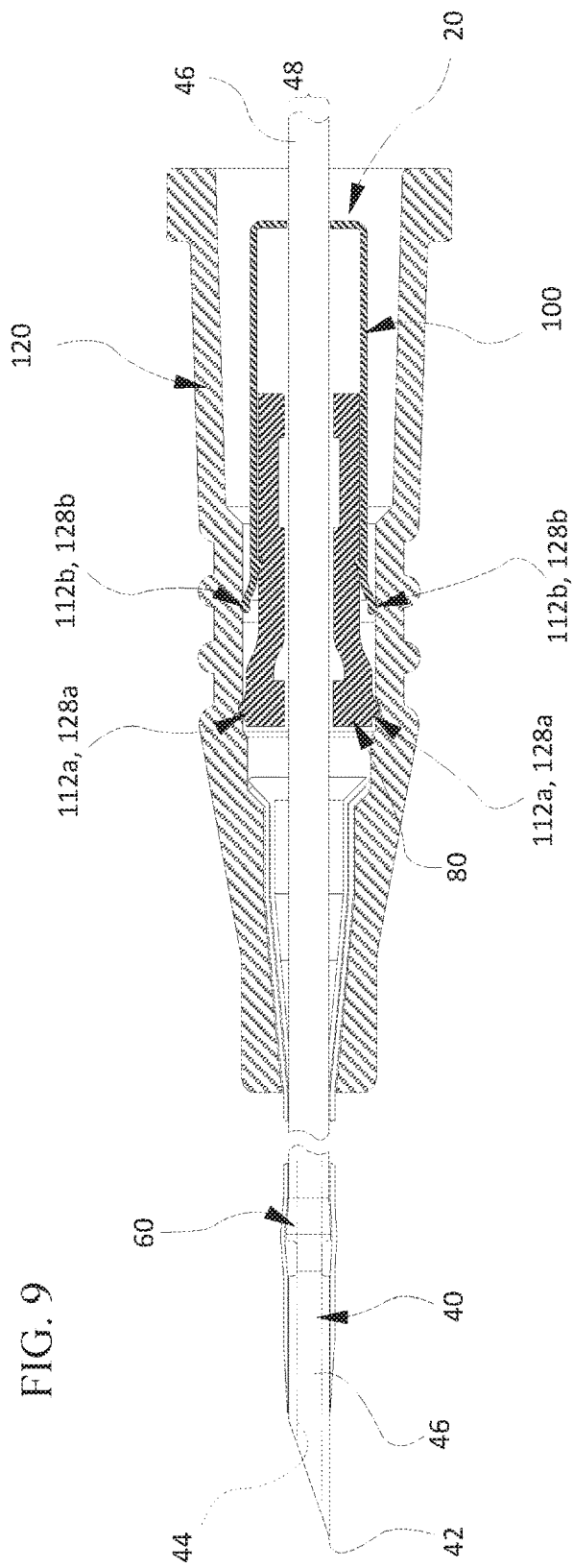
FIG. 9 illustrates a partial cut-away plan view of a representative embodiment of a catheter adapter in which interlock components are formed on the inner and outer housings of the bi-directional cannula feature capture mechanism.

FIG. 9 illustrates an example where the interlock components 112a, 112b are formed on both the inner housing 80 and the outer housing 100. In such cases, corresponding interlock surfaces 128a, 128b can be formed in appropriate locations within the adapter's lumen. Accordingly the capture mechanism can be configured in various different ways to interlock with the adapter.

In addition to the previously described embodiments of the bi-directional needle feature capture mechanism, the capture mechanism may be modified in any suitable manner that allows it to fulfill its intended purpose. For instance, while FIG. 5B shows an embodiment in which the distal ends 94 and 104 of both the inner housing 80 and the outer housing 100, respectively, extend past the needle's distal tip 42, in other embodiments, only the distal end of the outer housing or inner housing extend past the needle's distal tip when the needle is in the shielded position. For instance, FIG. 6A shows a representative embodiment in which only the outer housing 100 is configured to shield the needle's tip 42 when the proximal engagement surface 72 contacts the proximal mating component 84 and the needle's tip 42 is moved proximally past the outer housing's distal end 104. In contrast, FIG. 6B shows a representative embodiment in which only the inner housing 80 is configured to extend distally past and shield the needle's tip 42 when the feature's proximal engagement surface 72 contacts the inner housing's proximal mating component 84.

In another example of how the capture mechanism can be modified, FIG. 6B shows the that instead of comprising a canister-like object (as shown in FIG. 6A), the outer housing 100 may simply include a ring-like structure that is adapted to receive the inner housing 80.

The described bi-directional needle feature capture mechanism can be used in any suitable manner. By way of non-limiting illustration, FIG. 7A shows that before the needle 40 is inserted into a patient's blood vessel (not shown), the needle 40 extends axially through the inner 80 and outer 100 housings and through the distal tip 124 of the catheter adapter 120. Additionally, FIG. 7A shows that before the needle 40 is inserted into the blood vessel, the needle's feature 66 is disposed distal to the inner housing's distal end 94. Moreover, FIG. 7A shows the inner housing 80 is disposed within the outer housing 100, distal to the inner housing stop 106.

Figure 7C:
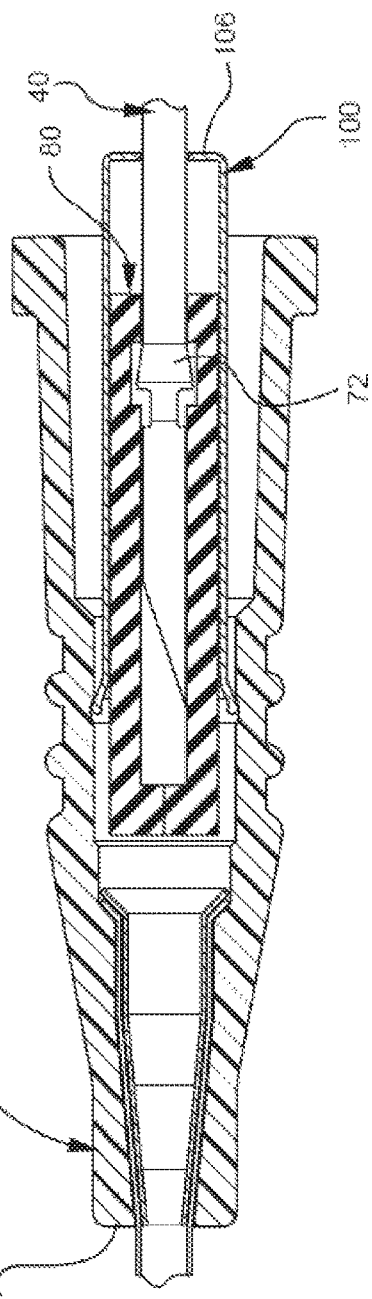
Figure 7D:
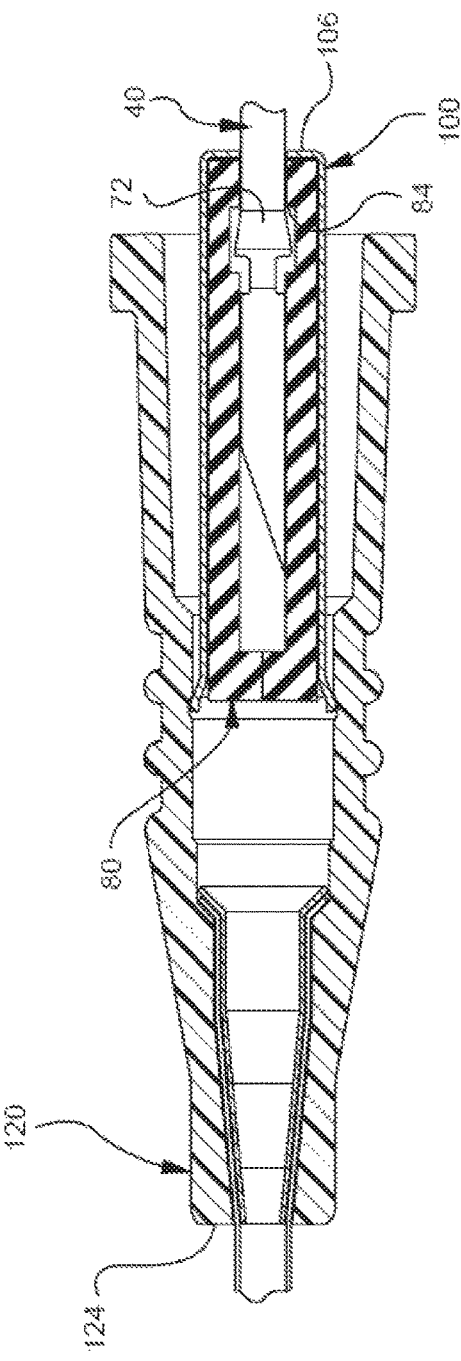
Figure 7E:
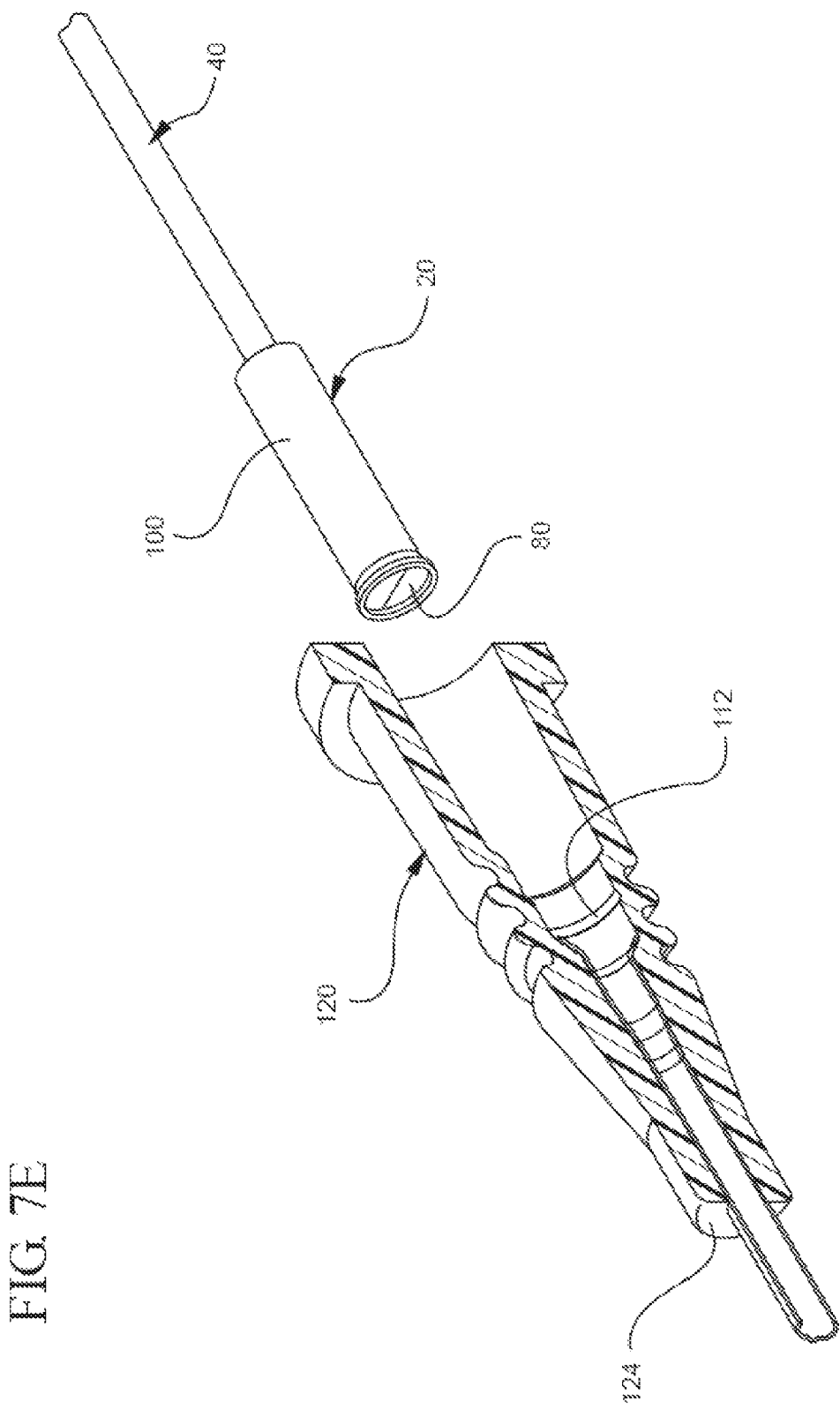

After the needle 40 has been inserted into the blood vessel, FIGS. 7B and 7C show the needle 40 is withdrawn proximally into the inner housing 80 while the position of the inner housing 80 relative to the outer housing 100 remains substantially unchanged. Once the feature's proximal engagement 72 contacts the proximal mating component 84, FIG. 7D shows the inner housing 80 moves proximally with respect to the outer housing 100 until reaching the inner housing stop 106. Finally, FIG. 7E shows that once the needle 40 is irreversibly locked in the capture mechanism 20, the outer housing 100 can be pulled proximally so as to uncouple from the adapter 120. Accordingly, the operator may use the catheter and safely dispose of the needle.

The described capture mechanism and associated methods may offer several advantages over certain prior art needle shielding devices. For example, because the described capture mechanism captures the needle's feature, the mechanism does not require transverse barrier tip protection. Instead, as described above, the mechanism may include transverse barrier tip protection as a redundant safety feature to provide enclosed needle point coverage. In another example, because the capture mechanism captures the needle's feature primarily, and not the needle's tip, the capture mechanism may be relatively compact. This compact design may allow the entire capture mechanism to be contained within the lumen of the catheter adapter. Additionally, the compact design may allow the capture mechanism to be inexpensive to manufacture and to incorporate additional components, such as conventional or novel valving technologies for post-activation blood control.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter device, comprising:
    a bi-directional cannula feature capture mechanism comprising:
        an inner housing, wherein the inner housing comprises an elastomeric material, wherein the inner housing comprises a proximal cannula feature mating component and a distal cannula feature mating component;
        a catheter adapter;
        an outer housing, wherein the outer housing comprises a material that is less flexible than the elastomeric material, wherein an inner surface of the outer housing comprises at least one proximally-facing barb that gouges into the elastomeric material of the inner housing to thereby prevent the inner housing from translating distally through the outer housing while allowing the inner housing to translate proximally through the outer housing; and
        a cannula that extends into the inner housing, wherein the cannula comprises a distal tip and a cannula feature, wherein the cannula feature comprises a proximal engagement surface and a distal engagement surface, wherein when the cannula is retracted proximally within the inner housing, the proximal engagement surface contacts the proximal cannula feature to prevent the cannula feature from moving proximally out of the bi-directional cannula feature capture mechanism and the distal cannula feature mating component prevents the distal tip from moving distally out of the bi-directional cannula feature capture mechanism, thereby shielding the distal tip within the bi-directional cannula feature capture mechanism.

2. The catheter device of claim 1, wherein the distal cannula feature mating component contacts the distal engagement surface to prevent the distal tip from moving distally out of the bi-directional cannula feature capture mechanism.

3. The catheter device of claim 1, wherein the distal cannula feature mating component contacts the distal tip to prevent the distal tip from moving distally out of the bi-directional cannula feature capture mechanism.

4. The catheter device of claim 1, wherein, when the proximal engagement surface contacts the proximal cannula feature, the inner housing is positioned proximal to the at least one proximally-facing barb.

5. The catheter device of claim 4, wherein the material that is less flexible than the elastomeric material comprises metal.

6. The catheter device of claim 1, wherein the inner housing forms a needle port through which the cannula extends, the needle port also being formed of the elastomeric material to thereby wipe blood from the cannula as the cannula moves proximally through the needle port.

* * * * *